US012365007B2

(12) United States Patent
Winder et al.

(10) Patent No.: US 12,365,007 B2
(45) Date of Patent: Jul. 22, 2025

(54) ULTRASOUND TRANSDUCER FOR MEDICAL APPLICATIONS

(71) Applicants: SONOGEN MEDICAL, INC., Chevy Chase, MD (US); Alan Winder, Westport, CT (US); Robert Muratore, Huntington, NY (US)

(72) Inventors: Alan Winder, Westport, CT (US); Robert Muratore, Huntington, NY (US)

(73) Assignee: SONOGEN MEDICAL, INC., Chevy Chase, MD (US)

( * ) Notice: Subject to any disclaimer, the term of this patent is extended or adjusted under 35 U.S.C. 154(b) by 163 days.

(21) Appl. No.: 18/263,814

(22) PCT Filed: Feb. 1, 2021

(86) PCT No.: PCT/US2021/016100
§ 371 (c)(1),
(2) Date: Aug. 1, 2023

(87) PCT Pub. No.: WO2022/164459
PCT Pub. Date: Aug. 4, 2022

(65) Prior Publication Data
US 2024/0091811 A1    Mar. 21, 2024

(51) Int. Cl.
*B06B 1/02* (2006.01)
*A61N 7/00* (2006.01)
*B06B 1/06* (2006.01)

(52) U.S. Cl.
CPC .............. *B06B 1/0223* (2013.01); *A61N 7/00* (2013.01); *B06B 1/0607* (2013.01); *A61N 2007/0013* (2013.01)

(58) Field of Classification Search
CPC ....... B06B 1/0223; B06B 1/0607; A61N 7/00; A61N 2007/0013; A61N 2007/0004;
(Continued)

(56) References Cited

U.S. PATENT DOCUMENTS 5,402,793 A     4/1995  Guner et al.
5,590,858 A     1/1997  Chiang et al.
                (Continued)

FOREIGN PATENT DOCUMENTS

EP         1414521 B1     10/2005
JP      2014221409 A2     11/2014
                (Continued)

OTHER PUBLICATIONS

Liang, "UC Berkeley Electronic Theses and Dissertations", found on the internet at https://escholarship.org/uc/item/9kt7rObr, Spring 2020, 113 pages.
(Continued)

*Primary Examiner* — Hien N Nguyen
(74) *Attorney, Agent, or Firm* — F. CHAU & ASSOCIATES, LLC

(57) ABSTRACT

An ultrasound transducer assembly includes a housing; a wedge-shaped acoustic modal convertor (AMC) in the housing with a first surface exposed by an opening in the housing, and a second surface that meets the first surface at a tip located in the housing, and extends from the tip at an angle into the housing, wherein the second surface has a recessed portion formed therein, wherein the second surface of the AMC is oriented at a specific oblique angle to the first surface of the AMC; and a piezoelectric ultrasound transducer disposed in the recessed portion of the second surface of the AMC, wherein the piezoelectric ultrasound transducer is connected to an electrically tuned circuit that resonates at a specific frequency and has a finite bandwidth.

20 Claims, 9 Drawing Sheets

(58) Field of Classification Search
CPC .... A61N 2007/0017; A61N 2007/0056; A61B 8/4281; A61B 8/4444; A61B 8/0875
See application file for complete search history.

(56) References Cited

U.S. PATENT DOCUMENTS

| | | | |
|---|---|---|---|
| 5,738,098 A | 4/1998 | Brock-Fisher et al. | |
| 6,562,471 B1 | 4/2003 | Chandran et al. | |
| 2006/0106424 A1* | 5/2006 | Bachem | A61N 7/00 607/1 |
| 2007/0249969 A1* | 10/2007 | Shields, Jr. | A61N 7/00 601/2 |
| 2009/0131837 A1* | 5/2009 | Granville | A61N 7/00 601/2 |
| 2009/0306551 A1 | 12/2009 | De et al. | |
| 2014/0276069 A1 | 9/2014 | Amble et al. | |
| 2022/0184424 A1* | 6/2022 | Winder | A61N 7/00 |

FOREIGN PATENT DOCUMENTS

| | | | | |
|---|---|---|---|---|
| WO | WO-03013654 A1 * | 2/2003 | | A61N 7/00 |
| WO | 2007118224 | 10/2007 | | |
| WO | 2020112688 A1 | 6/2020 | | |
| WO | 2020154633 A1 | 7/2020 | | |

OTHER PUBLICATIONS

Supplementary European Search Report dated Aug. 16, 2024, in corresponding European Patent Application 21923532.2, 12 pages.
Office Action dated Oct. 1, 2024 in corresponding JP Patent Application No. 2023-571240, 10 pages.

\* cited by examiner

FIG. 4

Table 1

Electro-acousto properties of a Barrel Transducer: Pulser Model 5072PR; Energy Level 2 (26 micro-joules); Damping 3 (50 ohms); Gain -20 dB. [3]

| S/N | Center Frequency (kHz) | -6 db Bandwidth (kHz) | - 20 dB Pulsewidth (μsec) | $Z_{elect}$ (ohms/deg) |
|---|---|---|---|---|
| 0720-5985 | 950.4 | 437 | 5.5 | 49.6/+0.9 |
| 0720-5986 | 962.0 | 452 | 3.5 | 58.1/-5.7 |
| 0720-5988 | 954.5 | 439 | 5.4 | 50.9/-7.5 |

FIG. 6

Table 2

Test Results for Transducers, with 1.000 MHz Excitation at 24.0 Vpp and $z_{max}$ = 34.8 mm [4]

| S/N | MI (MPa/MHz$^{1/2}$) | Aer (cm$^2$) | Rbn |
|---|---|---|---|
| 0720-5985 | 0.13 | 1.78 | 2.90 |
| 0720-5986 | 0.13 | 1.70 | 2.93 |
| 0720-5988 | 0.12 | 1.74 | 2.71 |

ULTRASOUND TRANSDUCER FOR MEDICAL APPLICATIONS

CROSS-REFERENCE TO RELATED APPLICATION

This application is a National Phase of PCT application PCT/US2021/016100, filed on Feb. 1, 2021, in the U.S. Receiving Office, the contents of which are herein incorporated by reference in their entirety.

BACKGROUND

Technical Field

Embodiments of the disclosure are directed to an ultrasound transducer that produces shear waves that efficiently invokes a cascade of cellular functions to accelerate tissue healing.

Discussion of the Related Art

The use of ultrasound in the 0.5 to 2.0 MHz range to therapeutically treat tissue and bone injuries is known. Specific acoustic signal spatial, temporal, and frequency parameters have been determined that can accelerate the natural healing of tissue tears, bone breaks, and fractures.

SUMMARY

Embodiments of the disclosure provide an acoustic transducer that can exogenously and simultaneously apply both acoustic longitudinal and shear stress waves to the extracellular matrix (ECM) of a bone cell to increase its integrin response and thus, increase the associated mechano-biochemical conversion efficiency of the bone healing process.

According to an embodiment of the disclosure, there is provided an ultrasound transducer assembly that includes a housing; a wedge-shaped acoustic modal convertor (AMC) in the housing with a first surface exposed by an opening in the housing, and a second surface that meets the first surface at a tip located in the housing, and extends from the tip at an angle into the housing, wherein the second surface has a recessed portion formed therein, wherein the second surface of the AMC is oriented at a specific oblique angle to the first surface of the AMC; and a piezoelectric ultrasound transducer disposed in the recessed portion of the second surface of the AMC, wherein the piezoelectric ultrasound transducer is connected to an electrically tuned circuit that resonates at a specific frequency and has a finite bandwidth. The piezoelectric ultrasound transducer includes a back surface that is electroded with a metal plating in a uniform or elliptical pattern, that protrudes from the recessed portion and that is loaded with a material that controls a forward scattering amplitude and absorption cross-section, and a front surface inside the recessed portion that is also electrode. The front surface establishes a ground plane and includes a matching layer over the ground plane of one or more materials, and wherein a tuned ultrasound transducer transmits oblique acoustic waves of an electrical signal designed for bone fracture healing.

According to a further embodiment of the disclosure, the ultrasound transducer transmits acoustic waves at a resonant center frequency from 0.1 MHz to 10 MHz.

According to a further embodiment of the disclosure, the ultrasound transducer transmits acoustic waves at a frequency from 0.5 MHz to 2 MHz.

According to a further embodiment of the disclosure, the ultrasound transducer transmits acoustic waves for bone fracture healing at 1 MHz with a spatial average temporal average intensity of 30-60 mW/cm$^2$, a pulsewidth of 0.1-10 milliseconds, a duty cycle of 10-50%, and a pulse repetition frequency equal to or less than 10 KHz.

According to a further embodiment of the disclosure, the piezoelectric ultrasound transducer further includes one or more of a family of piezoelectric elements.

According to a further embodiment of the disclosure, the family of piezoelectric elements includes PZT-4, PZT-5H, PZT-7H and PZT-8.

According to a further embodiment of the disclosure, a composition of the embedded AMC includes a silicone rubber polymer and a thin-film silicone primer that bonds the silicone rubber polymer to non-silicone surfaces.

According to a further embodiment of the disclosure, the silicone rubber polymer includes one of RTV-60, RTV-31, RTV-88, RTV-511, RTV-560, or RTV-577, and the thin-film silicone primer includes one of SS4004P or SS4155.

According to a further embodiment of the disclosure, the silicone rubber polymer indicates a specific critical angle based upon the silicone rubber polymer's longitudinal and shear velocity based on Snell's Law and generates maximum shear waves in bone tissue.

According to a further embodiment of the disclosure, the maximum shear waves have a beam-nonuniformity ratio (BNR) of less than or equal to 6.0 for medical ultrasound applications.

According to a further embodiment of the disclosure, the maximum shear waves have a beam-nonuniformity ratio (BNR) of less than or equal to 5.0 for medical ultrasound applications.

According to a further embodiment of the disclosure, the maximum shear waves have a beam-nonuniformity ratio (Rbn) of less than or equal to 4.0 for medical ultrasound applications.

According to a further embodiment of the disclosure, the maximum shear waves have a beam-nonuniformity ratio (Rbn) of less than or equal to 3.0 for medical ultrasound applications.

According to a further embodiment of the disclosure, the maximum shear waves produce a Mechanical Index (MI) of less than or equal to 0.5 with 24V pp input into the transducer at 1 MHz frequency.

According to a further embodiment of the disclosure, the maximum shear waves produce a Mechanical Index (MI) of less than or equal to 0.2 with 24V pp input into the transducer at 1 MHz frequency.

According to a further embodiment of the disclosure, the ultrasound transducer includes an elliptical electrode pattern on the front face thereof that creates a circular effective radiating area in an oblique plane at an angle based on the major and minor axes and eccentricity of the ellipse and increases the spatial-temporal measurement accuracy at that angle.

According to a further embodiment of the disclosure, the tuned circuit is part of an output stage of a high efficiency transmitter power switching amplifier.

According to a further embodiment of the disclosure, the power switching amplifier includes one of a Class D, a Class E or a Class F configuration.

According to a further embodiment of the disclosure, the ultrasound transducer assembly includes a gel sensor that will partially reside in a micro-controller unit (MCU) and a processing circuit incorporated into the housing of the transducer that samples an amplitude and phase coherence at a surface of an AMC/skin interface and senses air bubbles in a coupling of the first surface of the AMC to biological tissue that indicates a non-transmission.

According to a further embodiment of the disclosure, the ultrasound transducer assembly includes an external test meter that integrates the sum of the spatial acoustic beam orientation of the ultrasound transducer with a conjugate surface of an externally applied AMC whose output is normalized and sent to the test meter to determine the total transmitted rms power.

BRIEF DESCRIPTION OF THE DRAWINGS

FIG. 4 is a table of measured electro-acousto properties of an ultrasound transducer according to an embodiment of the disclosure.

FIG. 6 is a table of common measures of non-thermal nonlinear ultrasound behavior in biological tissue, according to an embodiment of the disclosure.

DETAILED DESCRIPTION

Figure 1:
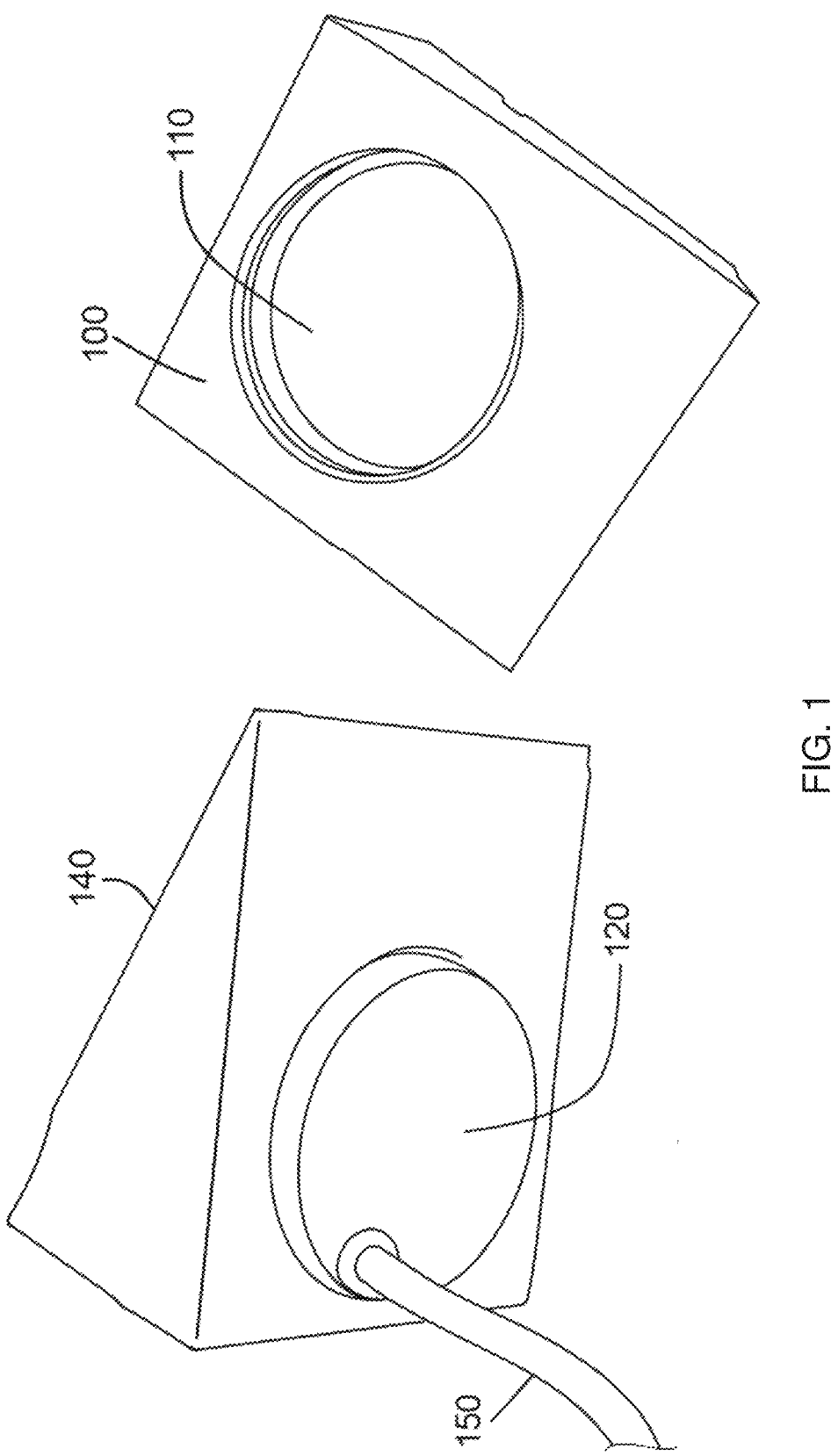
FIG. 1 is a photo of an acoustic modal converter (AMC), oriented to show its interior surface, and a second AMC applied externally over the transducer, according to an embodiment of the disclosure.

FIG. 1 is a photo of an acoustic modal converter (AMC) 100 test device. On the right side, the AMC 100 is oriented to show a recessed area 110 that can receive a transducer. The left side shows the AMC on its side, which shows a transducer 120 received in the recessed area 110 and the oblique angled surface 140 that is opposite to the transducer 120. A power cord 150 is attached to the transducer 120. This is the simplest approach to oblique beam steering. The oblique angle can control the relative amount of propagating longitudinal and shear energy in bone tissue, and the amount of heat energy generated.

According to an embodiment of the disclosure, to determine a balance between shear and longitudinal modes, an insonified biological structure is modeled as a parallel four-layer system, where the outermost three layers, i.e., skin, fat, and muscle, behave as viscous fluids, and the innermost fourth layer, which is bone, behaves as a viscoelastic solid. Bone tissue should be characterized with both viscous and elastic components to meaningfully influence bone fracture repair.

According to an embodiment, acoustic waves transmitted to the interior of the bone propagate as both shear waves and longitudinal waves, referred to herein as a bi-model acoustic signal (BMAS).

Snell's Law indicates that when a wave moves from a slower to a faster material, there is an incident angle, known as the first critical angle, which results in a 90 degree angle of refraction for the longitudinal wave. If the angle of incidence becomes greater than the first critical angle, the shear wave energy propagating into the material dominates the longitudinal wave energy and increases as the obliqueness increases. In most materials, there is also an incident angle that results in almost a 90 degree angle of refraction for the shear wave. This is referred to as the second critical angle.

Furthermore, in physical acoustics, when a plane wave is obliquely incident almost at the second critical angle, on an almost plane interface between a viscous fluid and a viscoelastic solid, such as bone, shear waves will dominate and propagate along and just below the periosteal surface of the bone. Noting that acoustic shear waves are more "lossy" than longitudinal waves, the spatial average-temporal average (SATA) intensity levels of shear waves require SATA levels to be increased by at least 10 dB/cm 2 in the 0.5-2 MHz region over those required for longitudinal waves, to increase healing efficiency.

Proof-of-concept (POC) torsional test results of adult rabbits that had surgically-induced bilateral fibular osteotomies showed that the test device 100 of FIG. 1, with BMAS excitation, according to an embodiment, was superior to a current U.S Food and Drug Administration (FDA)-approved device after undergoing treatment [1]. The primary shear wave mode in the test device was achieved with the external AMC 110, comprised of a wedge of silicone rubber with the oblique angle of 31.5 degrees, where bone growth stimulation (BGS) appeared to respond more favorably to periosteal healing than endosteal healing. An AMC according to an embodiment is composed of a silicone rubber room temperature vulcanized (RTV) composition having an acoustic impedance in the range of 1.30-1.90 MRayls.

According to an embodiment, an RTV material was selected because its acoustic impedance closely matches those of biological tissues of interest. In addition, an RTV material can be easily molded to produce an oblique angle that is close to the second critical angle for maximum shear content in the desired bone tissue. Although an embodiment uses an RTV-60 silicone rubber, embodiments are not limited thereto, and in other embodiments, others in the RTV family can also be used, such as but not limited to, RTV-31, RTV-88, RTV-511, RTV-560, or RTV-577. However, any material whose acoustic impedance closely matches that of biological tissues can be used for an AMC.

Figure 2:
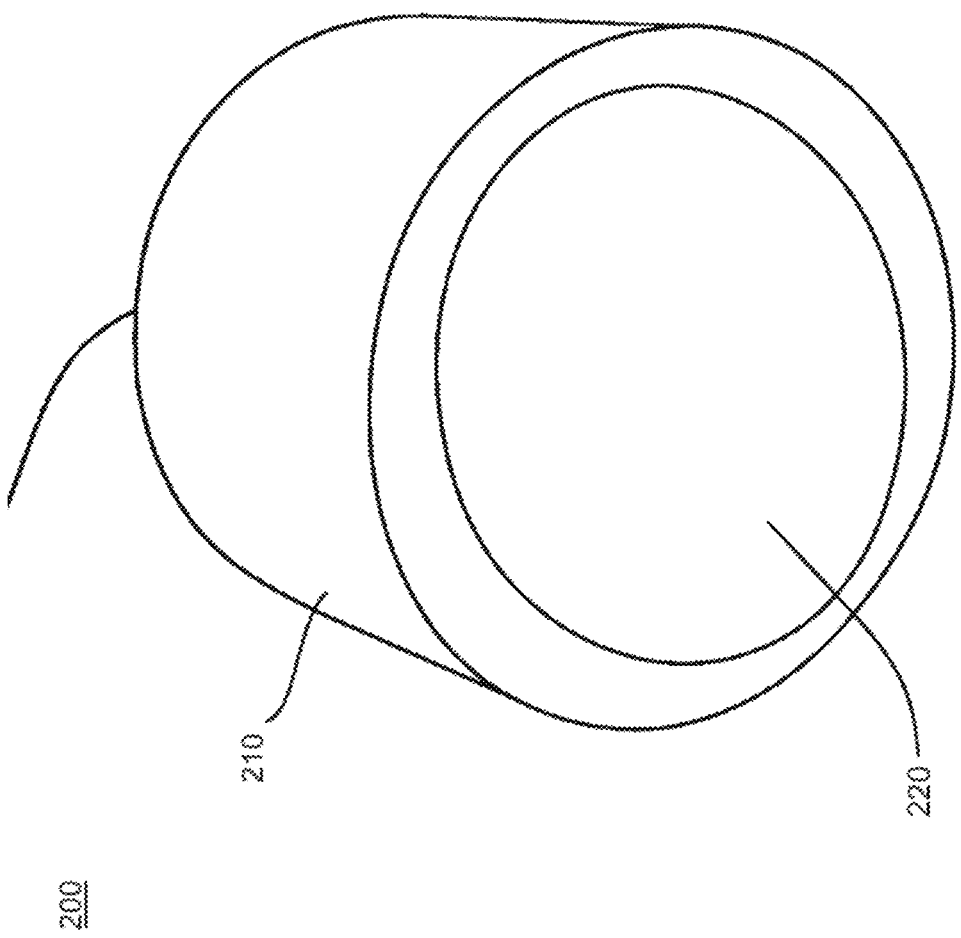
FIG. 2 is a photo of embedded AMC with an ultrasound transducer, according to an embodiment of the disclosure.

FIG. 2 depicts a barrel ultrasound transducer assembly 200 that includes a housing fixture 210, a radiating face with an embedded AMC wedge 220 of RTV-60 silicone rubber to which to produce an oblique transmission. A typical barrel ultrasound transducer assembly 200 shown in FIG. 2 is 1½-inches in diameter×1-inch in height, however, embodiments are not limited to these dimensions, and may be larger if needed. Although the housing fixture 210 shown in FIG. 2 is cylindrical in shape, with a circular cross section perpendicular to an axis of the cylinder, embodiments are not limited thereto, and the housing fixture 210 may have other cross sections in other embodiments, such as a rectangular, hexagonal, or pentagonal, etc. In addition, an exemplary material for fabricating a barrel ultrasound transducer assembly 200 is a hard, machinable, moldable plastic. The visible front surface of the embedded AMC wedge 220 corresponds to the oblique angled surface 140 of the AMC of FIG. 1. RTV-60 is a two-part compound that uses a 24-hour room temperature curing agent 0.5 wt. % DBTDL (dibutyltin dilaurate). The AMC wedge 220 includes a recessed region that corresponds to the recessed area 110 of FIG. 1 that is opposite to the face visible in FIG. 2, and a piezoceramic transducer is embedded in the recessed part of the AMC wedge 220. The piezoceramic transducer includes a non-silicone matching layer that requires application of a uniform thin adhesive film of a silicone primer, such as SS4004P or SS4155, to embed the transducer/matching layer into the AMC at the 31.5° angle. A thickness at the vertex should be a maximum of 2 mm, however, embodiments are not limited thereto. If the vertex thickness is thinner, it may produce a more fragile AMC and if thicker, additional power may be required to make up for the increase SATA loss in SATA due to RTV absorption. The beam pattern at 31.5° is scanned at a depth of about 8.5 mm from the center of the crystal. RTV-60 is a hospital grade elastomer, both non-toxic and impermeable to blood, that has the following measured properties at 1.0 MHz: an acoustic attenuation of 3.64 dB/cm; an acoustic impedance of 1.36 MRayls; a longitudinal velocity of 919 m/s; and a density of 1478 kg/m$^3$. These acoustic parameters are in excellent agreement with the reported Selfridge data [2].

Figure 3:
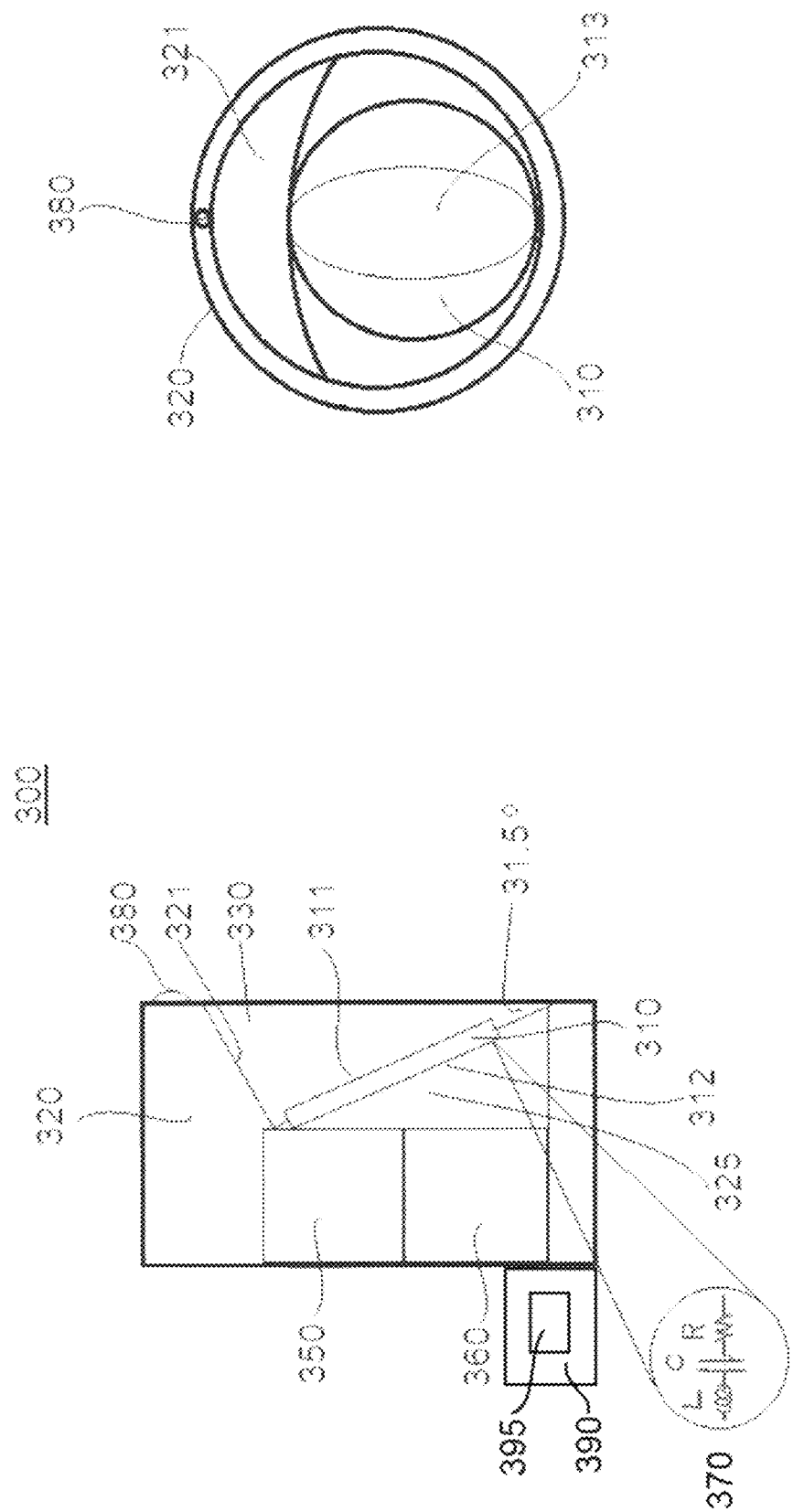
FIG. 3 shows several perspectives of an ultrasound transducer assembly using a plastic housing, according to an embodiment of the disclosure.

FIG. 3 shows a cross sectional view and a front view of an ultrasound transducer assembly 300 that includes a piezoelectric transducer 310 and a housing 320, according to an embodiment. The housing 320 contains the piezoelectric transducer 310 with an electroded ground plane covered with a ¼-wave matching layer 311 on a front surface thereof, on which is attached an embedded AMC 330.

The transducer element is slanted with respect to a front side of the housing fixture by an angle of 31.5°, which matches the wedge angle of the embedded AMC 330. The front view shows the transducer 310 with the AMC 330 removed, which also reveals the upper inner surface 321 of the housing 320. The indicator 380 on the housing indicates the direction of beam steering by the embedded AMC. The housing dimensions, disclosed above with reference to FIG. 2, permit transmission at the desired oblique angle without producing back-scattering interference.

A space 325 behind a back surface 312 of the transducer 310 is filled with air, but it is also well-known in the transducer design art that controlling the acoustic impedance of backing material can significantly affect detection and measurement parameter sensitivity. Exemplary, non-limiting piezoelectric elements include a PZT-4, a PZT-5H, a PZT-7H, and a PZT-8. The piezoelectric transducer 310 also includes a tuned electric circuit 370.

The back of the housing 320 includes cable housing 350 and a tuned electric circuit 370 connected to the cable housing 350 and to the transducer 310. The back surface 312 of the piezoelectric transducer 310 may be uniformly covered with an electrode pattern 312 or may be covered by an elliptical electrode pattern 313. The tuned circuit as shown in FIG. 3 is a series RLC network to transform the complex impedance of the transducer to a 50 ohms resistance that loads the previous output stage of the high-power switching amplifier in the driving transmitter. It is well-known in the electronics design art that the series-RLC shown can be replaced with equivalent pi ($\pi$) and T networks to facilitate specific operational considerations (i.e., balanced, unbalanced, heat dissipation, Q, etc.).

In some embodiments, the ultrasound transducer assembly 300 includes a gel sensor 395 that resides in a microcontroller unit (MCU) 390 and an additional processing circuit 360 that samples the amplitude and phase coherence at the front surface of the AMC/skin interface. The gel sensor 395 senses the effect of air bubbles that may interfere with the efficient coupling of the first surface of the AMC to biological tissue. An exemplary gel sensor 395 is disclosed in U.S. Pat. No. 6,261,249, the contents of which are herein incorporated by reference in their entirety.

The tuned electric circuit 370 in the gel sensor 395 may also be part of the output stage of the transmitter's power switching amplifier that may be, but is not limited to, one of a Class D, Class E, or Class F configuration. Separating the power MOSFET from the tuning output stage may benefit performance as related to battery size, heat generation and micro-miniaturization design in the accompanying transmitter to improve reliability.

The electro-acousto parameters for three tested ultrasound transducers are given in Table 1, shown in FIG. 4. FIG. 4 is a table of measured electro-acousto properties of the tested ultrasound transducers according to an embodiment of the disclosure, including transducer serial number (S/N), the center frequency, the −6 dB bandwidth, the −20 dB pulse length, and the electrical impedance $Z_{elect}$. An exemplary ultrasound transducer transmits acoustic waves at a resonant center frequency from 0.1 MHz to 10 MHz. Another exemplary ultrasound transducer transmits acoustic waves at a frequency from 0.5 MHz to 2 MHz. An ultrasound transducer according to an embodiment transmits acoustic waves for bone fracture healing at 1 MHz with a spatial average temporal average intensity of 30-60 mW/cm$^2$, a pulsewidth of 0.1-10 milliseconds, a duty cycle of 10-50%, and a pulse repetition frequency equal to or less than 10 KHz.

The silicone rubber polymer of the AMC 330 indicates the second critical angle based upon the silicone rubber polymer's longitudinal and shear velocity based on Snell's Law and generates maximum shear waves in bone tissue. In an embodiment, the maximum shear waves have a beam-nonuniformity ratio (BNR) of less than or equal to 6.0 for medical ultrasound applications. In an embodiment, the maximum shear waves have a beam-nonuniformity ratio (Rbn) of less than or equal to 4.0 for medical ultrasound applications. The maximum shear waves produce a Mechanical Index (MI) of less than or equal to 0.5 and apply 24V pp into the transducer at 1 MHz frequency. In an embodiment, the maximum shear waves have a beam-nonuniformity ratio (BNR) of less than or equal to 5.0 for medical ultrasound applications. In an embodiment, the maximum shear waves have a beam-nonuniformity ratio (Rbn) of less than or equal to 3.0 for medical ultrasound applications. The maximum shear waves produce a Mechanical Index (MI) of less than or equal to 0.2 and apply 24V pp into the transducer at 1 MHz frequency.

Figure 5A:
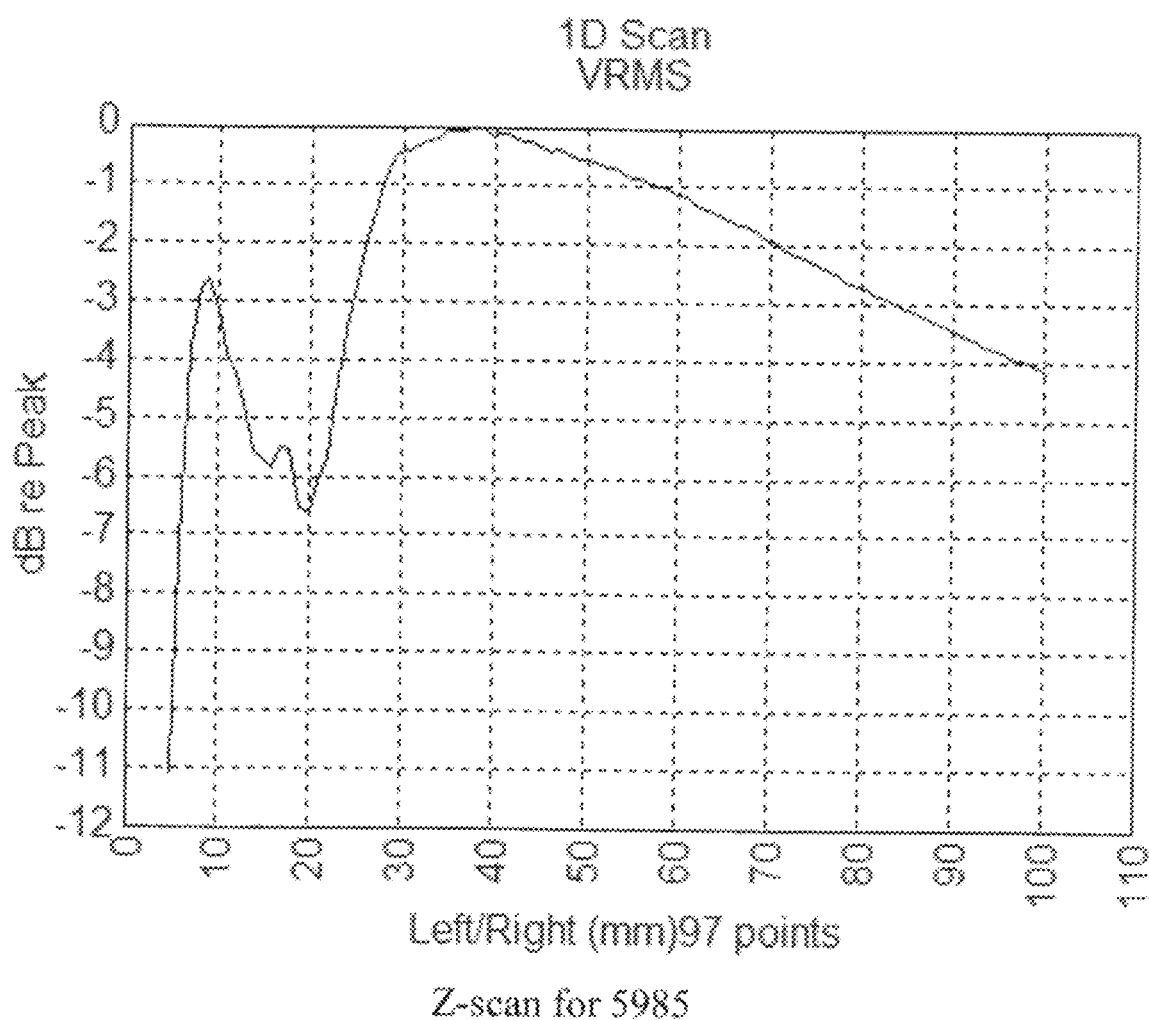
FIGS. 5A-C depicts: (A) a typical Z-scan; (B) a typical X-Y scan at 3 mm; and (C) a typical X-Y scan at 34.8 mm, according to an embodiment of the disclosure.
Figure 5B:
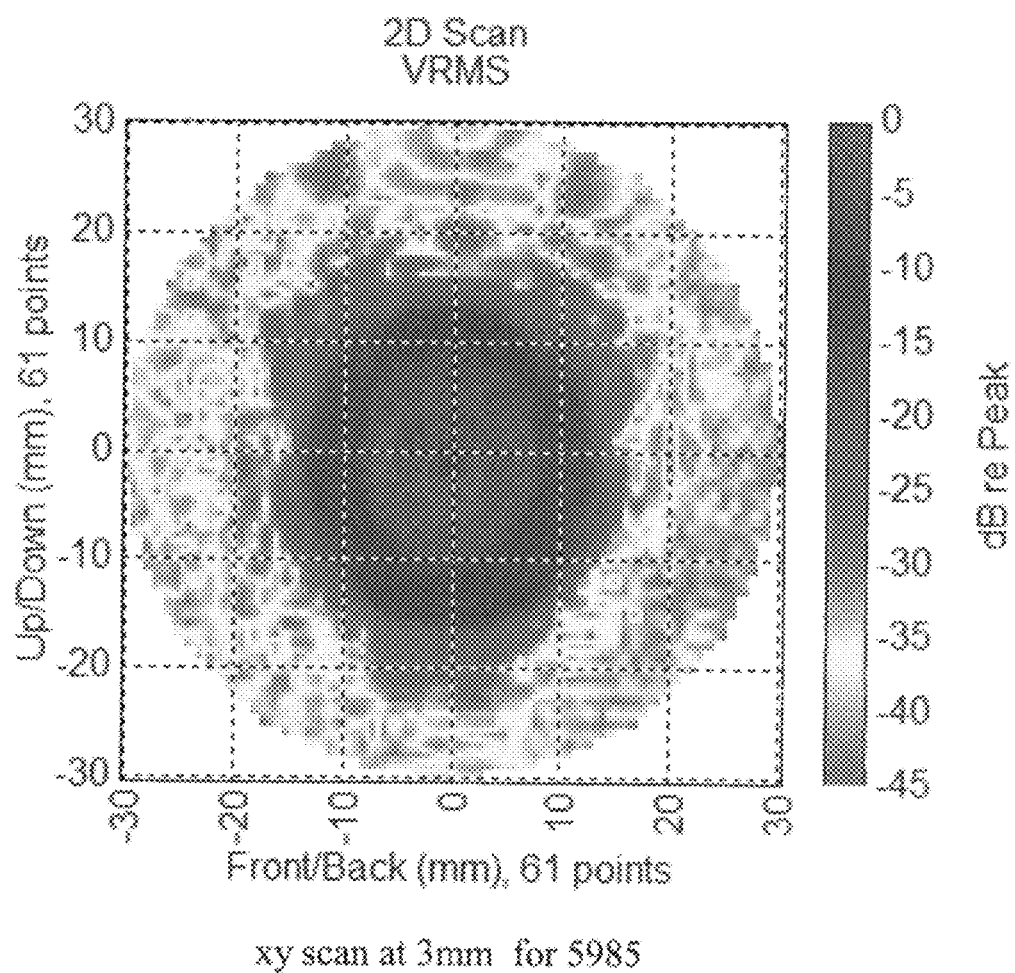
Figure 5C:
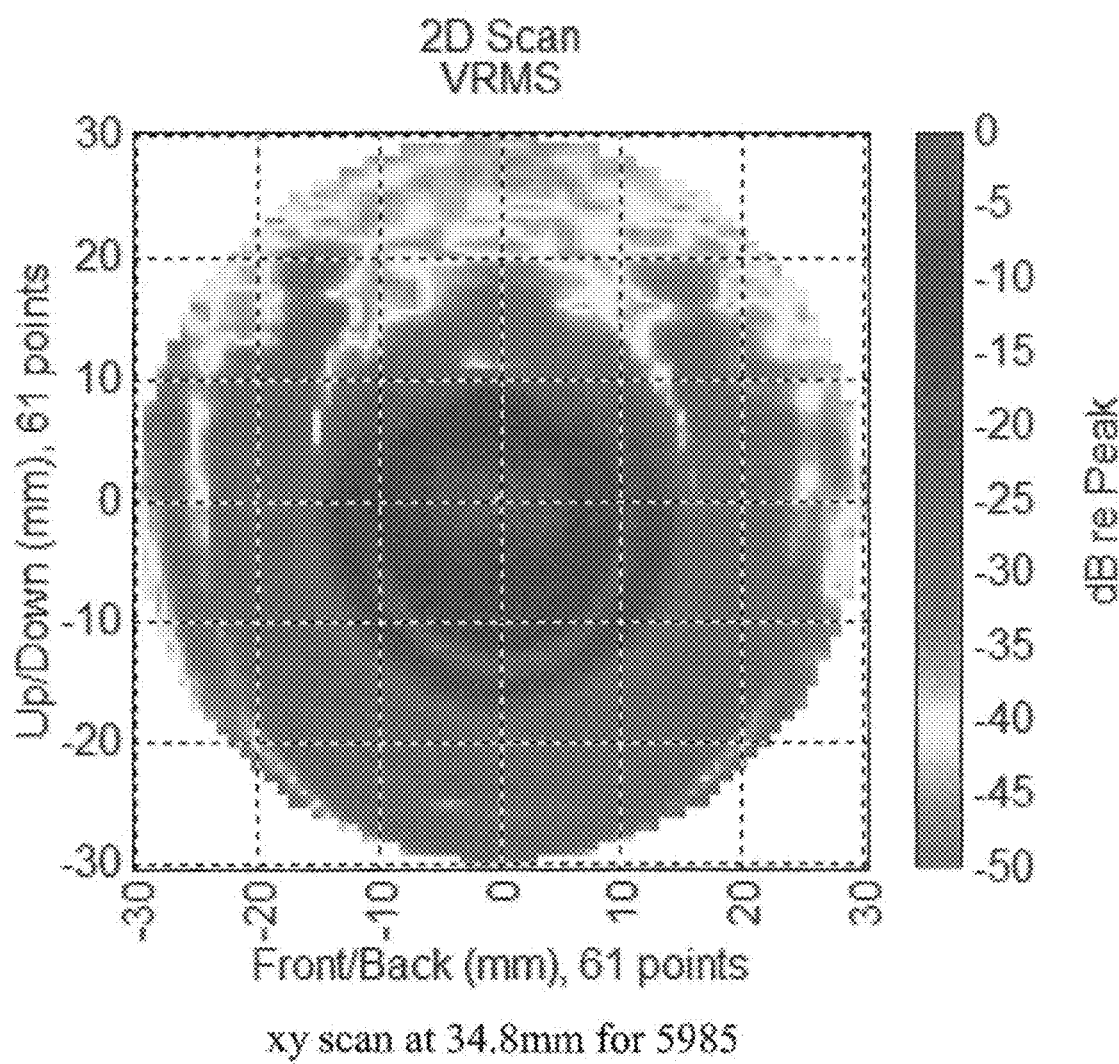

FIGS. 5A-C depict the beam plots of the root mean square voltage (VRMS) as a function of pixel count for a typical ultrasound transducer (S/N 5985) (A) a Z-scan; (B) an x-y scan at 3 mm; and (C) an x-y scan at 34.8 mm, according to an embodiment of the disclosure. The standard test protocol for determining the effective radiation area (ERA) or area for effective radiation (Aer) calls for a raster scan normal to the surface of the beam at 5 mm (for ERA) and 3 mm (for Aer) from the faceplate, respectively, which clinically is the patient contact surface; in many cases the latter is quite challenging to measure in practice.

For the oblique transmission, the following figures are typical for the ultrasound transducer designed and fabricated as representative by serial element no. 5985. FIG. 5A shows the Fresnel zone in a 1D-scan for the first 20 mm progressing to the in-phase Fraunhofer region with maximum at 34.8 mm and the in-phase wavelets slowly decaying with increasing propagation range as 1/z. As seen in FIGS. 5B-C, no acoustic "hot spots" were identified in the 2D-oblique beam plots for the tested transducers at z=3.0 and z=34.8 mm in the x-y plane.

The most distinguishing exception in these figures was the shape of the focused areas, circular in the near-field and elliptical in the far field. If a uniformly electroded face of a transducer is electroded in an elliptical pattern, a circular radiation beam pattern will be produced at a unique oblique plane in the far-field, at an angle based on the major and minor axes and eccentricity of the ellipse and that increases the spatial-temporal measurement accuracy at that angle. This will tend to produce a constant false alarm rate upon receive, and thus facilitate the detection of echoes and the extraction of information from a specific insonified region-of-interest (ROI) along the maximum response axis.

FIG. 6 shows Table 2, which is a table of common measures of non-thermal nonlinear ultrasound behavior in biological tissue for the tested ultrasound transducers, namely, transducer serial number, the mechanical index (MI; $MPa/MHz^{1/2}$), effective radiation area (Aer; $cm^2$), and the beam nonuniformity ratio (Rbn) that establish the safety standards of medical diagnostic and therapeutic ultrasound.

The ultrasound transducer in FIG. 2 was tested using a computer-controlled measuring system, with parameters given in Table 1, with excitation at resonant frequency of 1 MHz, a 6-dB bandwidth of 400 kHz, with a constant envelope, a pulsewidth of 200 microseconds, a pulse repetition frequency of 1 kHz, a duty cycle of 20%, and a drive voltage at the input to the transducer of 24.0 Vpp.

TECHNICAL BACKGROUND

Mechanical Index (MI)

The MI is a measure of the destructive behavior of ultrasound induced in biological tissue due to cavitation effects and is intended for B-mode short-pulse, low duty cycle (<2%) diagnostic imaging where high peak pressures are often obtained. The FDA requires that the MI for diagnostic and therapeutic devices be less than 0.7 in the unscanned mode, below which cavitation (theoretically) will not occur, and that the measured maximum value be indicated on the label of the device. It was assumed that stabilized pockets of gas or free bubbles exist in vivo, which clinically, is still not certain.

Beam Nonuniformity Ratio, (BNR, Rbn);(ERA/Aer)

The BNR/Rbn is a measure of possible acoustic hot spots in the radiated field and is defined as the [max $I_{SPTA}/I_{SATA}$], where [max $I_{SPTA}$] is at the acoustic axial distance of maximum pressure for unfocused transducers, at a point approximately equal to the (transducer diameter)$^2$/(4×wavelength λ). The ERA is the width of the beam intensity profile function at the −13 dB point, at a distance of 5 mm along the transducer axis and the Aer is the width at the −10 dB point, at a distance of 3 mm along the transducer axis.

Test Approach

Mechanical Index

The definition of MI is the ratio of the peak rare factional pressure ($p_r$, $MP_a$) that has been derated by 0.3 dB/MHz-cm, divided by the square root of the center signal spectra frequency (f; MHz):

$$MI = p_{r.3}/\sqrt{f} \quad (1)$$

The protocol for measuring the MI is as follows:
1. Measure the pulse intensity integral (PII) of the acoustic field along the transducer's MRA, represented as a series of maxima. The PII is computed as:

$$PII = \int_{T1}^{T2} p^2(t)dt/\rho c, \quad (2)$$

where ρ is the density and c is the speed of propagation of sound in the fluid.
2. Measure the negative pressure at the position of the maximum PII.
3. Divide the pressure from (2) by the square root of the signal resonant frequency.

Beam Nonuniformity Ratio

The steered beam from the ultrasound transducer in water is at an angle of approximately 52.3° from the normal to the faceplate. Tests performed the raster scan on a plane as close as possible to the surface and calculated the ERA and Aer at 5 mm and 3 mm, respectfully. The FDA requires that the BNR or Rbn for therapeutic devices be less than 8.0 and that the measured maximum value be indicated on the label of the device.

The BNr and Rbn were computed using the following formulae (3-4):

$$BNR = I_{spta} \times ERA \times \cos\theta / Power \quad (3)$$

$$Rbn = I_{spta} \times Aer \times \cos\theta / Power \quad (4)$$

where the factor cos θ is referred to in sonar and radar as the obliquity factor, the $I_{spta}$ is the maximum intensity detected by the hydrophone in the field, and θ is the measured angle of the beam relative to the normal to the faceplate, i.e., the angle between the z-axis and the direction of propagation.

In actual beam plot measurements, the difference between the faceplate RTV material velocity (919 m/s) and water velocity (1492 m/s) leads to a refraction of the beam of approximately θ=52.3 degrees relative to the normal of the faceplate. The values of Aer in Table 2 include the obliquity factor cos 52.3 degrees (=0.6115).

The tested transducers produced an MI≤0.13. The 1992 AIUM-NEMA Standard proposed an acceptable value for MI of less than 0.7 in the unscanned mode, below which cavitation (theoretically) will not occur. Results of clinical research to date show that there are no adverse nonthermal biological effects if the MI is less than 0.5. [6]

The FDA and International Electrophysical Commission (IEC) require that the measured maximum value of the BNR and Rbn for therapeutic devices be less than 8.0 and that the measured maximum value be indicated on the label of the device. [5,6] The tested transducers produced a BNR≤5 and, from Table 2, Rbn≤3. Note that the MI will vary with the driving voltage whereas Aer and Rbn should be independent of the driving voltage, assuming the transducers operate in the linear regime of acoustic propagation. Using test conditions and methods described in IEC 1689, the Rbn results reported in Table 2 "achieved a measurement uncertainty (at the 95% confidence level) of +/−15%" [4].

In addition, the active elements can be made of composites of such materials with polymeric, void and/or metallic components. Moreover, active elements made of such materials can generate low frequency waves via flex tensional effects attainable with unimorphs, monomorphs, bimorphs, cymbals, moonies, thunders, rainbows, cerambows, etc., as known by those skilled in the art. In addition, the frequencies mentioned herein can be generated by mechanical vibrations of air molecules or molecules of a medium in contact with the human body using speakers, buzzers, tuning forks, and/or any nonactive mechanical vibrating elements being driven by the active elements mentioned above. Furthermore, the low osteogenic frequencies disclosed herein can also be generated by transducers made of micro-electromechanical ultrasonic transducers (MUTs). Examples of such MUTs include a capacitive microelectromechanical ultrasonic transducer (CMUT) and a piezoelectric microelectromechanical ultrasonic transducer (PMUT). The CMUT and PMUT can be stand-alone transducers or be integrated on an electronic circuit board driving such MUTs.

The AMC material can be a thermoplastic urethane rubber, a polyurethane, or a silicon rubber.

Figure 7:
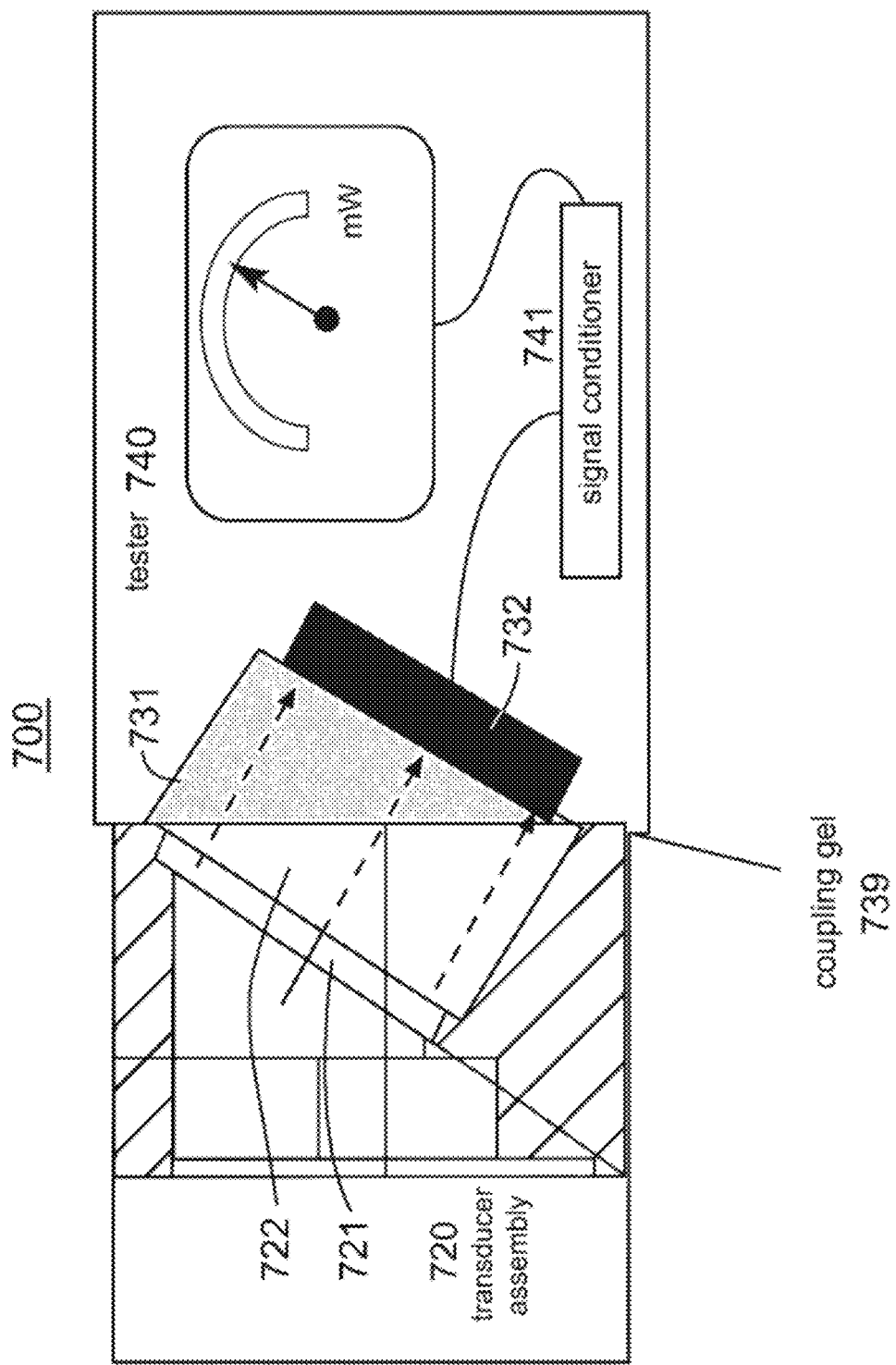
FIG. 7 depicts a means of measuring the transmitted root mean square (rms) acoustic power of an ultrasound transducer using a matching AMC rotated 180° with respect to the unit under test in order to normalize the path length of the beam, according to an embodiment of the disclosure.

FIG. 7 depicts an apparatus 700 for testing the rms acoustic power from an ultrasound transducer with an embedded AMC designated transducer assembly 720. FIG. 7 shows the internal cross-section of FIG. 2 that depicts piezoelectric transducer 721 and AMC 722 in contact with a respective matching AMC 732 that is rotated 180° with respect to the transducer 720 under test to normalize the path lengths of the beam. The two AMCs 722, 732 are separated by a coupling gel 739. A test assembly 700 includes a galvanometer test unit 740 and a signal conditioner 741 that may be comprised of a linear low noise preamplifier, a bandpass filter and a matching network to the tester 740 required for the accurate and stable measurement of the output signal from the test piezoelectric transducer 731.

In operation, transducer assembly 720 generates and propagates into AMC. Due to the fact that AMC 732 has been rotated 180° with respect to transducer assembly 720, the path lengths of the ultrasound energy at the output of AMC 731 are about the same, with minimal refraction through the AMC wedges 722, 732. Thus, the piezoelectric element 731 responds to the degree of rms acoustic energy coherence of the acoustic transmissions stimulating the piezoelectric element 731 to generate an electric signal that is measured by the calibrated galvanometer.

A design and fabrication approach according to an embodiment can be characterized by a least ten (10) unique features for obtaining bone stimulation for healing a fracture, as follows.

a. Acoustically and mechanically coupling the transducer and the AMC.
b. Employing the AMC to beam steer the acoustic waves to the biological tissue region-of-interest designated as the second critical angle by Snell's Law.
c. Embedding the acoustic modal converter (AMC), comprised of an RTV silicone polymer, such as RTV-60, into the transducer housing. Other materials in the RTV family can also be used.
d. Producing a beam-nonuniformity ratio (FDA; BNR) less than or equal to 5.0 for medical therapeutic ultrasound applications.
e. Producing a beam-nonuniformity ratio (IEC; Rbn) less than or equal to 3.0 for medical therapeutic ultrasound applications.
f. Producing a mechanical index (MI) less than or equal to 0.2 for both medical diagnostic and therapeutic applications.
g. Producing an elliptical transducer electrode pattern to create a circular effective radiating area for measuring the acoustic intensity in an oblique plane on it's MRA, thereby increasing measurement accuracy of spatial position parameters.
h. Including a tuning network that represents the output stage of a high efficiency switching power amplifier that resides in the driving transmitter, and may include the simple tuned inductor presently in the transducer. The increase in efficiency, in turn, can reduce battery requirements and facilitate micro-miniaturization design in the accompanying transmitter
i. Employing a gel sensor that will partially reside in a micro-controller unit (MCU) in the transmitter and an additional processing circuit in the transducer that samples the amplitude and phase coherence at the front surface of the AMC/skin interface.
j. Measuring the total rms acoustic power output from the transducer assembly under test 720 by employing a test assembly comprised of a conjugate AMC 731-signal conditioner 741 to normalize the beam pathlengths that will drive a calibrated galvanometer meter 740.

Although certain exemplary embodiments of the present disclosure have been specifically described herein, it will be apparent to those skilled in the art to which embodiments of the disclosure pertain that variations and modifications of the various embodiments shown and described herein may be made without departing from the spirit and scope of this disclosure.

REFERENCES

[1] Machado P; Li J.; Blackman R., Liu J-B; Kepler C; Fang T; Muratore R; Winder J; Winder, A; Forsberg F; *Comparison between clinically available low intensity pulsed ultrasound (LIPUS) and a novel bimodal acoustic signal system accelerating fracture healing*; submitted to TUFFC-manuscript no. 10470-2020; under review.
[2] Selfridge, A. R., *Approximate Material Properties in Isotropic Materials*, IEEE Transactions on Sonics and Ultrasonics, Vol. SU-32, No. 3, May 1985, 381-384.
[3] IEC 62359:2010+AMD1:2017 CSV: Ultrasonics-Field characterization—Test methods For the determination of thermal and mechanical indices related to medical indices related to medical diagnostic ultrasonic fields.
[4] IEC International Standard 61689 Edition 3.0 2013. Ultrasonics-Physiotherapy systems—Field specifications and methods of measurement in the frequency range 0.5 MHz to 5 Hz.
[5] *Mechanical Bioeffects from Diagnostic Ultrasound*: AIUM Consensus Statements, JUM, Vol 19 (No. 2); February 2000.
[6] *Special Section-Effects of Nonlinear Ultrasound Propagation on Output Display Indices*, JUM, Vol 18 (No. 1): 27-86, January 1999.

What is claimed is:

1. An ultrasound transducer assembly, comprising:
a housing;
a wedge-shaped acoustic modal convertor (AMC) in the housing with a first surface exposed by an opening in the housing, and a second surface that meets the first surface at a tip located in the housing, and extends from the tip at an angle into the housing, wherein the second surface has a recessed portion formed therein, wherein the second surface of the AMC is oriented at a specific oblique angle to the first surface of the AMC; and
a piezoelectric ultrasound transducer disposed in the recessed portion of the second surface of the AMC, wherein the piezoelectric ultrasound transducer is connected to an electrically tuned circuit that resonates at a specific frequency and has a finite bandwidth,
wherein the piezoelectric ultrasound transducer includes a back surface that is electroded with a metal plating in a uniform or elliptical pattern, that protrudes from the recessed portion and that is loaded with a material that controls a forward scattering amplitude and absorption cross-section, and a front surface inside the recessed portion that is also electroded,
wherein said front surface establishes a ground plane and includes a matching layer over the ground plane of one or more materials, and wherein a tuned piezoelectric ultrasound transducer transmits oblique acoustic waves of an electrical signal designed for bone fracture healing.

2. The ultrasound transducer assembly of claim 1, wherein said piezoelectric ultrasound transducer transmits acoustic waves at a resonant center frequency from 0.1 MHz to 10 MHz.

3. The ultrasound transducer assembly of claim 2, wherein said piezoelectric ultrasound transducer transmits acoustic waves at a frequency from 0.5 MHz to 2 MHz.

4. The ultrasound transducer assembly of claim 1, wherein said piezoelectric ultrasound transducer transmits acoustic waves for bone fracture healing at 1 MHz with a spatial average temporal average intensity of 30-60 $mW/cm^2$, a pulsewidth of 0.1-10 milliseconds, a duty cycle of 10-50%, and a pulse repetition frequency equal to or less than 10 KHz.

5. The ultrasound transducer assembly of claim 1, wherein the piezoelectric ultrasound transducer further includes one or more of a family of piezoelectric elements.

6. The ultrasound transducer assembly of claim 5, wherein the family of piezoelectric elements includes PZT-4, PZT-5H, PZT-7H and PZT-8.

7. The ultrasound transducer assembly of claim 1, wherein a composition of the AMC includes a silicone rubber polymer and a thin-film silicone primer that bonds the silicone rubber polymer to non-silicone surfaces.

8. The ultrasound transducer assembly of claim 7, wherein the silicone rubber polymer includes one of RTV-60, RTV-31, RTV-88, RTV-511, RTV-560, or RTV-577, and the thin-film silicone primer includes one of SS4004P or SS4155.

9. The ultrasound transducer assembly of claim 7, wherein the silicone rubber polymer indicates a specific critical angle based upon the silicone rubber polymer's longitudinal and shear velocity based on Snell's Law and generates maximum shear waves in bone tissue.

10. The ultrasound transducer assembly of claim 9, wherein the maximum shear waves have a beam-nonuniformity ratio (BNR) of less than or equal to 6.0 for medical ultrasound applications.

11. The ultrasound transducer assembly of claim 10, wherein the maximum shear waves have a beam-nonuniformity ratio (BNR) of less than or equal to 5.0 for medical ultrasound applications.

12. The ultrasound transducer assembly of claim 9, wherein the maximum shear waves have a beam-nonuniformity ratio (Rbn) of less than or equal to 4.0 for medical ultrasound applications.

13. The ultrasound transducer assembly of claim 12, wherein the maximum shear waves have a beam-nonuniformity ratio (Rbn) of less than or equal to 3.0 for medical ultrasound applications.

14. The ultrasound transducer assembly of claim 9, wherein the maximum shear waves produce a Mechanical Index (MI) of less than or equal to 0.5 with 24V pp input into the piezoelectric ultrasound transducer at 1 MHz frequency.

15. The ultrasound transducer assembly of claim 14, wherein the maximum shear waves produce a Mechanical Index (MI) of less than or equal to 0.2 with 24V pp input into the piezoelectric ultrasound transducer at 1 MHz frequency.

16. The ultrasound transducer assembly of claim 1, wherein the piezoelectric ultrasound transducer includes an elliptical electrode pattern on the front face thereof that creates a circular effective radiating area in an oblique plane at an angle based on a major and a minor axes and eccentricity of the ellipse and increases a spatial-temporal measurement accuracy at that angle.

17. The ultrasound transducer assembly of claim 1, wherein the tuned circuit is part of an output stage of a high efficiency transmitter power switching amplifier.

18. The ultrasound transducer assembly of claim 13, wherein the power switching amplifier includes one of a Class D, a Class E or a Class F configuration.

19. The ultrasound transducer assembly of claim 1, further comprising a gel sensor that will partially reside in a micro-controller unit (MCU) and a processing circuit incorporated into the housing of the piezoelectric ultrasound transducer that samples an amplitude and phase coherence at a surface of an AMC/skin interface and senses air bubbles in a coupling of the first surface of the AMC to biological tissue that indicates a non-transmission.

20. The ultrasound transducer assembly of claim 1, further comprising an external test meter that integrates a sum of the spatial acoustic beam orientation of the piezoelectric ultrasound transducer with a conjugate surface of an externally applied AMC whose output is normalized and sent to a test meter to determine a total transmitted rms power.

* * * * *